US012560545B2

(12) United States Patent
Shi

(10) Patent No.: US 12,560,545 B2
(45) Date of Patent: Feb. 24, 2026

(54) COLORIMETRIC MEASUREMENT OF FLUDIOXONIL

(71) Applicant: Syngenta Crop Protection AG, Basel (CH)

(72) Inventor: Yanxiang Shi, Greensboro, NC (US)

(73) Assignee: Syngenta Crop Protection AG, Basel (CH)

( * ) Notice: Subject to any disclaimer, the term of this patent is extended or adjusted under 35 U.S.C. 154(b) by 698 days.

(21) Appl. No.: 17/997,605

(22) PCT Filed: May 6, 2021

(86) PCT No.: PCT/US2021/031022

§ 371 (c)(1),
(2) Date: Oct. 31, 2022

(87) PCT Pub. No.: WO2021/226305

PCT Pub. Date: Nov. 11, 2021

(65) Prior Publication Data

US 2023/0221260 A1 Jul. 13, 2023

Related U.S. Application Data

(60) Provisional application No. 63/020,642, filed on May 6, 2020.

(51) Int. Cl.

| | |
|---|---|
| ***G01N 21/78*** | (2006.01) |
| ***C07D 405/04*** | (2006.01) |
| *G01N 21/75* | (2006.01) |

(52) U.S. Cl.
CPC .......... *G01N 21/78* (2013.01); *C07D 405/04* (2013.01); *G01N 2021/755* (2013.01)

(58) Field of Classification Search
CPC .. G01N 21/78; G01N 2021/755; G01N 31/22; C07D 405/04; A01P 3/00; A01N 43/36
See application file for complete search history.

(56) References Cited

U.S. PATENT DOCUMENTS

| | | | |
|---|---|---|---|
| 4,395,494 | A | 7/1983 | Bodart et al. |
| 2009/0221619 | A1 | 9/2009 | Cornish et al. |
| 2009/0297571 | A1 | 12/2009 | Cornish et al. |

FOREIGN PATENT DOCUMENTS

| | | | |
|---|---|---|---|
| WO | 2018/222750 | A1 | 12/2018 |

OTHER PUBLICATIONS

International Search Report for PCT/US2021/031022 mailed Aug. 12, 2021.

*Primary Examiner* — Lyle Alexander
*Assistant Examiner* — Dwan A Gerido
(74) *Attorney, Agent, or Firm* — R. Kody Jones

(57) ABSTRACT

A process for determining the fludioxonil content in a liquid medium by performing a color reaction with [4-(dimethylamino)phenyl]methanol (p-DAB) or 4-Dimethylaminocinnamaldehyde (DMACA) and an acid in the presence of fludioxonil and obtaining a colorimetric reading for the resulting mixture after a period of time.

11 Claims, No Drawings

COLORIMETRIC MEASUREMENT OF FLUDIOXONIL

RELATED APPLICATION INFORMATION

This application is a 371 of International Application No. PCT/US2021/031022, filed 6 May 2021, which claims priority to U.S. Application No. 63/020,642, filed 6 May 2020, the contents of which are incorporated herein by reference herein.

The present technology relates to the a process for determining the fludioxonil content in a liquid medium by performing a color reaction with [4-(dimethylamino)phenyl] methanol (p-DAB) or 4-Dimethylaminocinnamaldehyde (DMACA) and an acid in the presence of fludioxonil and obtaining a colorimetric reading for the resulting mixture after a period of time.

The present technology further relates to the a process for determining the fludioxonil content in a liquid medium by performing a color reaction with p-DAB or DMACA, and an acid in the presence of fludioxonil and obtaining a colorimetric reading for the resulting mixture after a period of time and creating reference samples with known fludioxonil content using the same methodology to compare the color of the liquid medium to the reference sample.

A reference sample as used herein means one or more colorimetric samples, or colorimetric references, having a known concentration of fludioxonil.

A period of time as used herein means a finite time period greater than zero.

The process of the present technology employs as reagents an indictor and an acid.

The first reagent, the indicator, is [4-(dimethylamino) phenyl]methanol (p-DAB) (CAS #1703-46-4) or 4-Dimethylaminocinnamaldehyde (DMACA) (CAS #20432-35-3) which are known, and commercially available, chemical compounds.

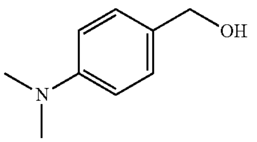

p-DAB

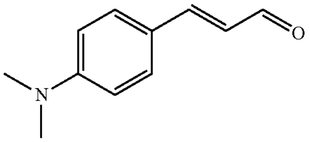

DMACA

Concentrations of p-DAB range from 0.1-20 g/100 mL solvent. Preferred concentrations of p-DAB range from 0.4-5 g/100 mL solvent and 0.4-2.5 g/100 mL solvent. Additional preferred concentrations of p-DAB include 2.5, 2, 1, and 0.4 g/100 mL solvent. Concentrations of DAMCA range from 0.1-20 g/100 mL solvent. Preferred concentrations of DAMCA range from 0.4-5 g/100 mL solvent and 0.4-2.5 g/100 mL solvent. Additional preferred concentrations of DAMCA include 2.5, 2, 1.25, and 0.4 g/100 mL solvent.

The solvent generally includes the second reagent, an acid, and includes both strong and weak acids. Non-limiting examples of acids suitable as the second reagent include hydrochloric acid, hydrobromic acid, hydroiodic acid, triflic acid, chloric acid, perchloric acid, nitric acid, sulfuric acid, oxalic acid, sulfurous acid, hydrogen sulfate ion, benzoic acid, methanoic (formic) acid, acetic acid, nitrous acid, hydrofluoric acid, and phosphoric acid.

The solvent is generally present in an amount to dissolve the indicator. By way of example, when at 2.5 g pDAB/100 mL solvent, the solvents that can dissolve the indicator include: 85% phosphoric acid:water=9:1 to 4:1 (v/v); 85% phosphoric acid:ethanol=4:1 (v/v); 85% phosphoric acid: methanol=4:1 (v/v); and 6 M hydrochloric acid.

Generally, any desired concentration of fludioxonil may be measured. Common concentration ranges of fludioxonil include 50 to 1000 ppm, 50 to 500 ppm, and 100 to 500 ppm.

EXAMPLE 1

Seven reference samples containing known concentrations of fludioxonil were prepared in laboratory tubes by mixing SCHOLAR® SC in the volumes shown in Table 1 with 50 ml of water. Scholar® SC is a well-known and commercially available fungicide sold by Syngenta Crop Protection and contains 20.4 w/w % fludioxonil (1.92 lb fludioxonil per gallon).

TABLE 1

| Reference Sample # | Scholar ® SC (μL) | Water (mL) | Reference Sample Conc. |
|---|---|---|---|
| 1 | 25 | 50 | 100 ppm |
| 2 | 37.5 | 50 | 150 ppm |
| 3 | 50 | 50 | 200 ppm |
| 4 | 62.5 | 50 | 250 ppm |
| 5 | 75 | 50 | 300 ppm |
| 6 | 87.5 | 50 | 350 ppm |
| 7 | 125 | 50 | 500 ppm |

An indicator solution comprising 2.5 g of p-DAB, 100 ml 85% phosphoric acid, and 5 mL of water was combined in a container thoroughly combined into solution.

1 mL of each refence sample are added to individual laboratory tubes (e.g. centrifuge tube or standard test tube) and combined with 1 mL of the indicator solution. The tubes are shaken to mix the solutions and placed in heating block at 95° C. for 1 hour. The result is a color concentration refence spectrum.

In practice a "sample solution" would also be created concurrently with the reference spectrum. The sample solution is the solution that a person is determining the fludioxonil concertation in, e.g., a water bath containing fludioxonil. The test proceeds in the same manner as the reference samples—1 mL of the sample solution is added to a test tube with 1 mL of indicator solution, the tube is shaken to mix the solution and placed in heating block at 95° C. for 1 hour.

The color of the sample solution is then compared by eye-sight, or by a colorimeter, to a reference sample to determine the fludioxonil concentration of the sample solution.

The present technology also includes a kit for performing the colorimetric analysis as described herein. The kit may include standard solutions of fludioxonil. The kit may also include a series of standard solutions, disposable pipets, test tubes (including small tube such as Eppendorf tubes or Corning tubes), gloves, goggles, tube rack, indicator (such as p-DAB or DAMCA), acid solvent; and written instructions.

The invention claimed is:

1. A method of performing a color reaction in the presence of fludioxonil in a liquid medium, the method comprising:

mixing an indicator selected from at least one of [4-(dimethylamino)phenyl]methanol and 4-dimethylaminocinnamaldehyde with an acid and fludioxonil wherein the acid includes at least one of phosphoric acid, sulfuric acid, nitric acid, hydrochloric acid, acetic acid, carbonic acid, hydrofluoric acid, citric acid, oxalic acid, or boric acid.

2. The method of claim 1, wherein the indicator is [4-(dimethylamino)phenyl]methanol.

3. The method of claim 2, wherein the acid is phosphoric acid, sulfuric acid, nitric acid, hydrochloric acid, acetic acid, carbonic acid, hydrofluoric acid, citric acid, oxalic acid or boric acid.

4. The method of claim 1, wherein the fludioxonil is present in an aqueous medium.

5. The method of claim 1, further comprising heating the mixture at 95° C. for a period of time.

6. The method of claim 5, where the period of time is one hour.

7. The method of claim 1, further comprising obtaining a colorimetric reading after a period of time for the mixture.

8. The method of claim 3, further comprising obtaining a colorimetric reading after a period of time for the mixture.

9. The method of claim 6, further comprising comparing the colorimetric reading to a reference sample.

10. A kit comprising:

a. [4-(dimethylamino)phenyl]methanol or 4-Dimethylaminocinnamaldehyde b. an acid; and c. fludioxonil wherein the acid includes at least one of phosphoric acid, sulfuric acid, nitric acid, hydrochloric acid, acetic acid, carbonic acid, hydrofluoric acid, citric acid, oxalic acid, or boric acid.

11. The kit of claim 10, further comprising:

a. one or more container(s); and b. a pipette.

* * * * *